(12) United States Patent
Tubis et al.

(10) Patent No.: US 6,508,009 B1
(45) Date of Patent: Jan. 21, 2003

(54) GEMSTONE MEASUREMENT APPARATUS

(76) Inventors: Semyen Tubis, 404 W. 7th St. Suite 1226, Los Angeles, CA (US) 90014; Igor Borisov, 404 W. 7th St. Suite 1226, Los Angeles, CA (US) 90014

( * ) Notice: Subject to any disclaimer, the term of this patent is extended or adjusted under 35 U.S.C. 154(b) by 0 days.

(21) Appl. No.: 09/662,724

(22) Filed: Sep. 15, 2000

(51) Int. Cl.[7] ................................................ G01B 5/00
(52) U.S. Cl. .............................. 33/549; 33/555; 33/783
(58) Field of Search ........................ 33/549, 555, 555.1, 33/679.1, 783, 784, 792, 793, 794

(56) References Cited

U.S. PATENT DOCUMENTS

| | | | |
|---|---|---|---|
| 3,166,851 A | * | 1/1965 | Shirakura et al. .............. 33/793 |
| 3,863,351 A | * | 2/1975 | Kalen ........................... 33/549 |
| 4,035,922 A | | 7/1977 | von Voros |
| 4,106,240 A | | 8/1978 | DeBartolo |
| 4,229,883 A | | 10/1980 | Kobashi |
| 4,326,336 A | * | 4/1982 | Hreha .......................... 33/555 |
| 4,845,646 A | | 7/1989 | Marquis et al. |
| 5,148,612 A | | 9/1992 | Walser et al. |
| 5,193,685 A | | 3/1993 | Trevithick |
| 5,424,830 A | * | 6/1995 | Andrychuk ................... 356/30 |
| 6,219,932 B1 | * | 4/2001 | Whitmore ..................... 33/549 |
| 6,253,459 B1 | * | 7/2001 | Barnhill ........................ 33/549 |

* cited by examiner

*Primary Examiner*—Diego Gutierrez
*Assistant Examiner*—Madeline Gonzalez
(74) *Attorney, Agent, or Firm*—Michael A. Painter

(57) ABSTRACT

An improved gemstone measuring apparatus includes a pair of linearly aligned measurement flanges used to determine the linear dimensions of a gemstone alone a plurality of axes. One of the measurement flanges is linearly moveable relative to the other. A measurement member translates the distance between the measurement flanges to display indicia responsive thereto. A rotatable support platform is coupled to the housing intermediate the measurement flanges, the axis of rotation thereof being co-extensive with a measurement flange. The gemstone whose dimensions are to be measured is disposed upon the rotatable support platform intermediate the measurement flanges. The rotatable platform is positioned to align the gemstone axis being measured with the axis of alignment of the measurement flanges.

8 Claims, 1 Drawing Sheet

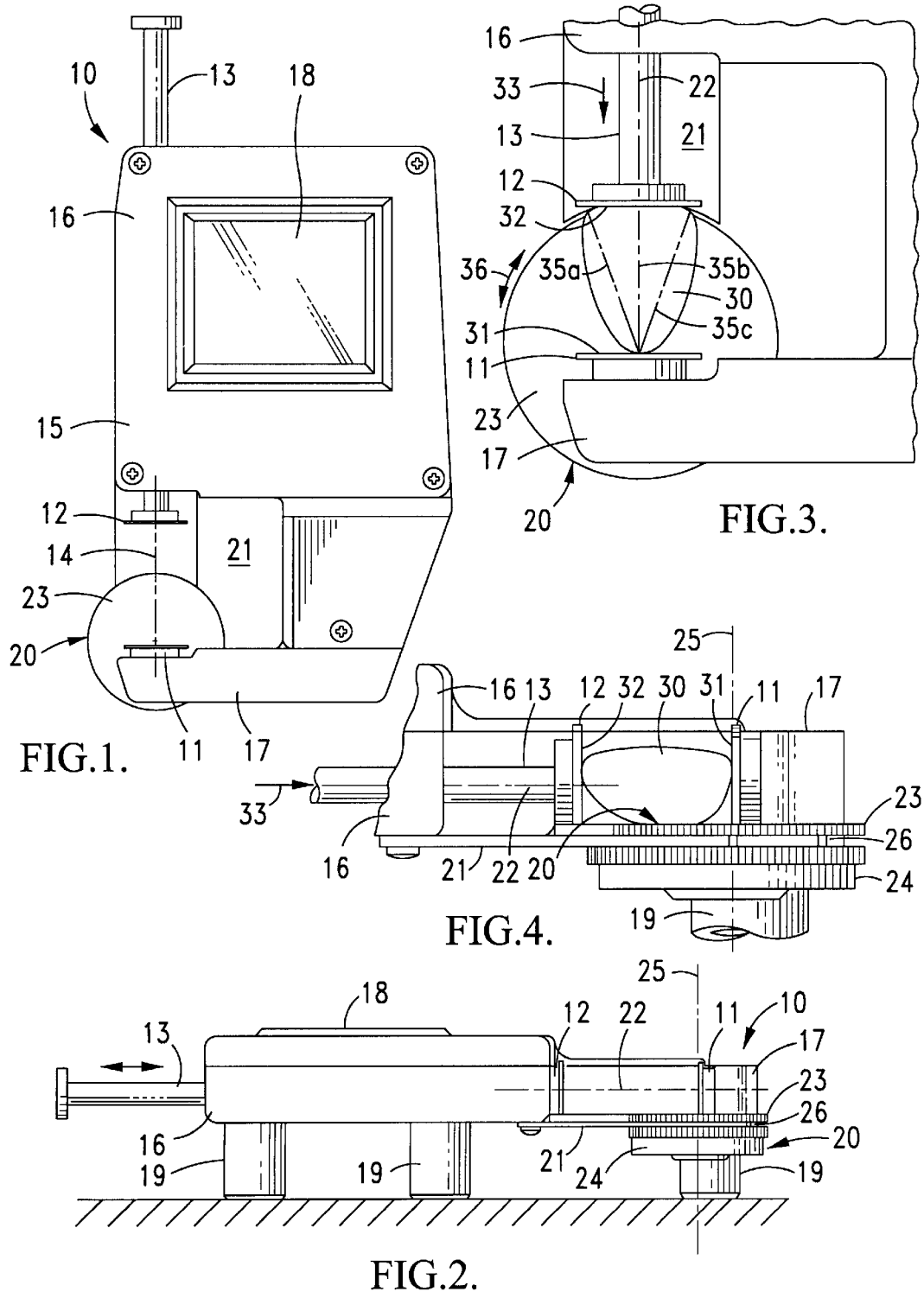

GEMSTONE MEASUREMENT APPARATUS

BACKGROUND OF THE INVENTION

1. Field of the Invention

The present invention generally relates to measuring instruments and, more particularly, to measuring instruments for gemstones which permit measurement along multiple axes without manual intervention.

2. Prior Art

Gemstones such as diamonds, emeralds and rubies are classified according to weight and shape. The weight of a gemstone may be determined by measuring one to three dimensions of the gemstone with a set of calipers and then referring to appropriate tables for the corresponding weight. The measurement of a gemstone was classically taken through the use of mechanical calipers which employ either spring-loaded caliper jaws or a thumbwheel control to place the caliper jaws adjacent the respective surfaces of the gemstone.

Manufacturers of jewelry incorporating gemstones have long recognized the necessity to be able to accurately determine the physical size and therefore the value of gemstones. This necessity is created by the frequent need to determine the weight of the gemstone or to properly measure dimensions for specific designs. In conventional instruments used to measure linear dimensions, a vernier scale or dial indicator is generally used. However, this category of instruments is inadequate because of the probability of misreading the typical analog display due to reading errors and human error in that the user is required to interpret mechanically measured dimensions. Such conventional measuring instruments are also inadequate in that the primary scale of measurement is based upon a fixed calibration of the instrument.

The instruments disclosed in the prior art which are employed for measuring the physical dimensions of gemstones exhibit additional inadequacies. Gemstones must be measured along multiple of axes in order to provide the information necessary to determine actual size and value. Where these measurements are attempted by manually repositioning the gemstone, this step will inject the added problems of misalignment of the gemstone and the unnecessary expenditure of time. These problems are not in any way addressed by the conventional measuring instruments disclosed in the prior art.

The measuring instruments disclosed in the prior art have progressed through the use of digital displays. The devices are generally referred to as caliper apparatus. A caliper apparatus disclosed by the prior art utilizes a magnescale in which magnetic calibrations are provided on a magnetic tape and a signal produced due to the movement of the scale relative to the magnetic tape. This is sensed to measure dimension. Another caliper device employs a linear encoder in which light is directed toward an optical measuring device in which light is reflected from a first member and received by a second member of the device. Reflected light is sensed to measure dimension. In yet another caliper device, a rotary encoder is employed in which a rotatable first member is rotated relative to a rotatable second member and bright and dark patterns of light are sensed to measure dimension. In all these cases, the problem related to the manual interpretation of a measurement is replaced by a digital display which eliminates reading errors and human error. However, these devices continue to be inadequate for the measurement of gemstones since the measurement of the gemstone along multiple axes has required manual intervention by the user.

Another device disclosed by the prior art is one which is hand held, but uses spring-loaded caliper jaws to measure the dimensions of multiple axes of the gemstone. Although this device also provides means for automatically calculating the gemstone weight, it suffers from the same inadequacies as other devices described in the prior art. To measure multiple axes of a gemstone, these devices all require the manual manipulation of the gemstone to permit measurement of the relevant dimensions thereof.

The present invention substantially resolves those inadequacies inherent in those devices disclosed in the prior art. The present invention employs known means for determining the dimensions of a selected axis of a gemstone. The member used for measurement can be mechanically adjusted caliper jaws which provide for an analog or digital display, or even those which utilize magnetic or optical measuring devices. The improvement provided by the present invention relates to the ability to measure multiple axes of the gemstone without manual contact between the user and the gemstone. A rotatable platform is provided upon which the gemstone is mounted. The axis of the rotatable platform is co-extensive with an edge of the gemstone. Once the gemstone is mounted on the rotatable platform, the measurement means are placed adjacent the surfaces of the gemstone through which the measured axis extends. To obtain measurements for other axes of the gemstone, the platform is rotated to a selected axis of the gemstone and the measurement repeated. As a result, all axes of the gemstone relevant to determining the commercial weight thereof can be measured without physical interaction between the user and the gemstone.

SUMMARY OF THE INVENTION

The present invention comprises an improved measurement apparatus for measuring the dimensions of small objects in general, and gemstones in particular. The novel structural features of the present invention can be employed with any number of conventional measurement apparatus. For the purpose of example only, and without limiting the scope of the invention, the present invention employs a measurement apparatus pursuant to which selected dimensions are measured between a pair of measurement flanges. One of the measurement flanges is fixed, the second measurement flange being moveable to receive the gemstone irrespective of size. A rotatable platform is disposed adjacent the fixed measurement flange, the axis of the rotatable platform adapted to be perpendicular to the dimension of the gemstone being measured. In operation, the gemstone is placed on the rotatable platform, the axis of the gemstone to be measured to be aligned with the axis of the aligned measurement flanges. A plurality of dimensions of the gemstone may be measured merely by altering the position of the rotatable platform about its axis. The measurement of all relevant dimensions of the gemstone may be performed without any manual contact between the user and the gemstone.

It is therefore an object of the present invention to provide an improved gemstone measurement apparatus.

It is another object of the present invention to provide an improved gemstone measurement apparatus which permits measurement along multiple axes of the gemstone through the use of a rotatable support platform for the gemstone.

It is still yet another object of the present invention to provide an improved gemstone measurement apparatus which permits multiple measurements of the gemstone in the absence of any movement of the gemstone relative to the rotatable support platform.

It is still yet another object of the present invention to provide an improved gemstone measurement apparatus which is simple and inexpensive to fabricate.

The novel features which are believed to be characteristic of the invention, both as to its organization and method of operation, together with further objectives and advantages thereof, will be better understood from the following description considered in connection with the accompanying drawing in which a presently preferred embodiment of the invention is illustrated by way of example. It is to be expressly understood, however, that the drawing is for the purpose of illustration and description only, and is not intended as a definition of the limits of the invention.

BRIEF DESCRIPTION OF THE DRAWINGS

FIG. 1 is a top, plan view of the present invention illustrating the gemstone support platform.

FIG. 2 is a side elevation view of the present invention illustrating the relative position of the rotatable support platform and the measurement flanges FIG. 3 is an enlarged, partial top plan view of an exemplary gemstone in place upon the rotatable support platform intermediate the measurement flanges.

FIG. 4 is an enlarged, partial side elevation view of a gemstone in place upon the rotatable support platform shown in FIG. 3.

DESCRIPTION OF THE PRESENTLY PREFERRED EMBODIMENT

An understanding of the improved gemstone measurement apparatus can be best gained by reference to FIGS. 1 and 2. The purpose of the present invention is to provide the ability to measure a plurality of dimensions of a gemstone in order to determine the corresponding weight thereof or to properly size a gemstone for a specific design. The improvement of the present invention over those devices disclosed in the prior art specifically relates to the ability to take measurements of gemstones without requiring physical contact between the gemstone and the user. A preferred embodiment of the present invention is identified by reference numeral 10. As shown in FIG. 1 and FIG. 2, gemstone measurement apparatus 10 employs measurement means which comprises a fixed measurement flange 11 and an aligned, moveable measurement flange 12. Measurement flanges 11 and 12 are aligned with one another along a common axis 14. As shown, moveable measurement flange 12 is axially secured to spring-loaded shaft 13. When a force is exerted shaft 13 toward fixed measurement flange 11, the distance between moveable measurement flange 12 and fixed measurement flange 11 will be reduced. When the force on shaft 13 is removed, the spring-loaded, resilient force will cause the distance between measurement flanges 11 and 12 to increase. Although the preferred embodiment of the present invention is illustrated in FIGS. 1 and 2, it is understood the structure and function of measurement flanges 11 and 12 could be replaced by other conventional structures such as mechanical calipers which employ either spring-loaded caliper jaws or a thumbwheel control, the selection being a matter of choice.

Shaft 13 is resiliently mounted within housing 15, the resilient member in the form of a spring or the like (not shown). Housing 15 comprises a display base 16 and an extension arm 17 which are integral with one another. Fixed measurement flange 11 is secured to extension arm 17 in alignment with shaft 13 and moveable measurement flange 12 along axis 14. Integral display base 16 and extension arm 17 are adapted to be horizontally positioned upon a table or like surface by a plurality of secured mounting legs 19.

The preferred embodiment of the present invention provides a digital display 18 to present indicia responsive to the distance between fixed and moveable measurement flanges 11 and 12. The digital circuits used to measure the position of shaft 13 and the distance between fixed and moveable measurement flanges 11 and 12 are well known in the art to which the present invention pertains. The improvement provided by the present invention over the measurement apparatus disclosed in the prior art relates to the ability to make a plurality of measurements of a gemstone's dimensions without requiring manual contact between the user and the gemstone.

A gemstone is adapted to be supported upon a rotatable support platform 20. A fixed, planar member 21 is secured to the bottom surface of display base 16. Planar member 21 extends from the bottom surface of display base 16 to extension arm 17 and is in parallel, spaced relation to the aligned shaft 13, fixed measurement flange 11 and moveable flange 12. A preferred embodiment of rotatable support platform 20 consists of a circular disk 23 which is disposed on one side of planar member 21 and control member 24 which is disposed on the opposite side of planar member 21. Although the preferred structure of rotatable support platform 20 combines the coupled structure of circular disk 23 and control member 24, it is understood the scope of the present invention includes the use of a single member which can both support the gemstone and be rotated to permit measurement of a plurality of gemstone axes. Control member 24 and disk 23 are axially coupled to one another by a plurality of bracing members 26 to along the common axis 25 thereof frictionally engaging the opposed surfaces of planar member 21 therebetween. The axis 25 of the coupled disk 23 and control member 24 is perpendicular to axis 22 of aligned shaft 13, fixed measurement flange 11 and moveable measurement flange 12. Axis 25 of the coupled platform 23 and control member 24 is co-planar with the surface of fixed measurement flange 11.

The operation of the present invention can be best understood by reference to FIG. 3 and FIG. 4. As stated, the purpose of the present invention is to provide the ability to measure a plurality of gemstone dimensions in order to derive the corresponding weight for the gemstone. Referring now to FIG. 3 and FIG. 4, the present invention is illustrated having an exemplary gemstone 30 mounted upon disk 23 of rotatable support platform 20. An edge of gemstone 30 is placed adjacent surface 31 of fixed measurement flange 11. Force is disposed upon shaft 13 in a direction identified as reference numeral 33 until surface 32 of moveable measurement flange 12 contacts gemstone 30.

FIG. 3 illustrates three exemplary axes 35a, 35b and 35c which define a measurement which may be used to determine the corresponding weight of gemstone 30. In the orientation shown in FIG. 3, axis 35b is aligned with the common, aligned axis 22 of shaft 13, fixed measurement flange 11 and moveable measurement flange 12. As stated, measurement of the dimension of the gemstone 30 may be made when surfaces 31 and 32 contact the gemstone along a respective axis 35a, 35b and 35c. In the configuration shown in FIG. 3, the distance between surfaces 31 and 32 define the dimension of the gemstone along axis 35b. To measure the dimension of gemstone 30 along either axis 35a or 35c, control member 24 and coupled disk 23 are rotated in the appropriate direction identified by reference numeral 36. When axis 35a or 35c is aligned with axis 22 of shaft 13, fixed measurement flange 11 and moveable measurement flange 12, a force is exerted on shaft 13 in the direction shown by reference numeral 33 until moveable measurement flange 12 is adjacent gemstone 30 in the manner shown in FIG. 4. The distance between surfaces 31 and 32 provide data responsive to the gemstone dimension being measured.

It can therefore be seen the present invention provides a measurement apparatus for gemstone which substantially overcomes the inadequacies inherent in those devices disclosed by the prior art. Measurements of a gemstone 30 may be taken from the corresponding weight is determined. Once gemstone 30 is mounted upon disk 23 of rotatable support platform 20, there need no physical contact between the user and gemstone 30 during the measurement process.

We claim:

1. A gemstone measuring apparatus for measuring a gemstone along selected axes comprising:
   (a) a housing and a first measurement flange secured to the housing, said first measurement flange being defined by a first longitudinal axis and including a planar surface perpendicular to said longitudinal axis;
   (b) a second measurement flange coupled to the housing linearly moveable relative to and axially aligned with the longitudinal axis of the first measurement flange, said second measurement flange including a planar surface perpendicular to the longitudinal axis of said first measurement flange;
   (c) rotatable support means coupled to said housing intermediate said first and second measurement flanges, for rotatably supporting and orienting a selected axis of the gemstone relative to the aligned first and second measurement flanges; and
   (d) measurement means coupled to said first and second measurement flanges for providing indicia responsive to the linear distance between said first and second measurement flanges.

2. A gemstone measuring apparatus as defined in claim 1 wherein said rotatable support means comprises:
   (a) a disk having a surface perpendicular to the planar surfaces of said first and second measurement flanges and in parallel spaced relation to a selected axis of the gemstone and rotatable relative to said housing and having an axis of rotation co-extensive with the planar surface of said first measurement flange; and
   (b) a control member axially aligned with and secured to said disk whereby the surface of said disk is angularly rotatable relative to the planar surface of said first measurement flange.

3. A gemstone measuring apparatus as defined in claim 1 wherein said measurement means includes a digital display.

4. A gemstone measuring apparatus as defined in claim 1 wherein said second measurement flange is resiliently biased with respect to said first measurement flange.

5. A gemstone measuring apparatus for measuring gemstones along selected axes comprising:
   (a) a housing including a display base and an opposed extension arm;
   (b) a first measurement flange having a longitudinal axis and having a planar surface perpendicular to said longitudinal axis secured to said extension arm in opposition to the display base;
   (c) a second measurement flange slidably coupled to the display base of said housing in opposition to the extension arm and being linearly moveable relative to and axially aligned with the longitudinal axis of the first measurement flange;
   (d) rotatable support means coupled to said housing intermediate said display base and said extension arm for rotatably supporting and orienting a selected axis of the gemstone relative to the axially aligned first and second measurement flanges, said rotatable support means comprising:
      (1) a circular disc having a surface adapted to receive the gemstone and being perpendicular to the planar surfaces of said first and second measurement flanges, said disc being in parallel, spaced relation to the axes of the gemstone and being rotatable relative to the display base and having an axis of rotation co-extensive with the planar surface of said first measurement flange; and
      (2) a control member axially aligned with and secured to said circular disc whereby the surface of said disc is angularly rotatable relative to the planar surface of said first measurement flange; and
   (e) measurement means coupled to said first and second measurement flanges for providing indicia responsive to the linear distance between said first and second measurement flanges along a selected axis of the gemstone.

6. A gemstone measuring apparatus as defined in claim wherein said first and second measurement flanges each include planar surfaces which are parallel to each other and perpendicular to the axis of said first and second measurement flanges.

7. A gemstone measuring apparatus as defined in claim 6 wherein said display base includes digital display means for displaying the distance between the planar surfaces of said first and second measurement flanges.

8. A gemstone measuring apparatus as defined in claim 5 wherein said second measurement flange is resiliently biased in opposition to the parallel surface of said first measurement flange.

* * * * *